United States Patent [19]

Müller et al.

[11] Patent Number: 6,084,091
[45] Date of Patent: Jul. 4, 2000

[54] PROCESS FOR PURIFYING, STABILISING OR ISOLATING NUCLEIC ACIDS FROM BIOLOGICAL MATERIALS

[75] Inventors: Oliver Müller; Rainer Deuter, both of Dortmund, Germany

[73] Assignee: Max-Planck-Gesellschaft Zur Forerung Der Wissenschaften E.V., Germany

[21] Appl. No.: 09/011,567

[22] PCT Filed: Aug. 14, 1996

[86] PCT No.: PCT/EP96/03595

§ 371 Date: Feb. 11, 1998

§ 102(e) Date: Feb. 11, 1998

[87] PCT Pub. No.: WO97/07239

PCT Pub. Date: Feb. 27, 1997

[30] Foreign Application Priority Data

Aug. 16, 1995 [DE] Germany .................. 195 30 132

[51] Int. Cl.[7] .................. C07H 21/00; C07H 19/00
[52] U.S. Cl. .................. 536/25.4; 536/27.1; 435/6; 435/91

[58] Field of Search .................. 536/25.4, 27.1; 435/6, 91

[56] References Cited

FOREIGN PATENT DOCUMENTS

| 0189280 | 7/1986 | European Pat. Off. . |
|---|---|---|
| 0393744 A1 | 4/1989 | European Pat. Off. . |
| 0389063 A2 | 9/1990 | European Pat. Off. . |
| 0574267 | 12/1993 | European Pat. Off. . |

OTHER PUBLICATIONS

QIAGEN Product Lit., 1995.
Fearon and Vogelstein, Cell, vol. 61, pp. 759–766, 1990.

*Primary Examiner*—James O. Wilson
*Assistant Examiner*—Howard Owens
*Attorney, Agent, or Firm*—Fulbright & Jaworski, LLP

[57] ABSTRACT

The invention relates to a method of purifying, stabilizing and/or isolating nucleic acids contained in biological matter, wherein an adsorption matrix is added to a nucleic-acid-containing specimen of biological matter in order to bind contaminants.

44 Claims, No Drawings

PROCESS FOR PURIFYING, STABILISING OR ISOLATING NUCLEIC ACIDS FROM BIOLOGICAL MATERIALS

BACKGROUND OF THE INVENTION

This invention relates to a method of stabilizing, purifying and/or isolating nucleic acids contained in biological matter by removing contaminants, eg, substances which damage nucleic acids and inhibit enzymatic reactions. The method is especially suitable for analyzing, detecting or isolating nucleic acids in stool specimens. A reagents kit for implementing the method of the invention is also disclosed.

Numerous examples from various fields of research underline the impedance of analyzing nucleic acids contained in biological matter in which there are contaminants that damage nucleic acids during storage and inhibit the enzymatic manipulation thereof, eg, by amplification. If the nucleic acids contained in the biological matter are to be used for further analyses, it is thus important that these contaminants are only present in very low concentrations or are removed entirely from the specimen.

The analysis of nucleic acids contained in fecal specimens is of particular importance. The principal medical application is the detection of tumor-specific changes in nuclear DNA from fecal matter. Such changes can serve as a parameter for the early diagnosis of tumors in the digestive tract. The identification of bacterial and viral pathogens contained in fecal specimens by means of test methods based on nucleic acids is likewise becoming increasingly more important.

A method of isolating nucleic acids from fecal matter is disclosed in WO 93/20235. This method, however, results in only small yields of nucleic acids, and DNA-damaging and/or PCR-inhibiting substances are not removed. This means that the isolated DNA cannot be stored for long, and the amplification of specific gene sections to be analyzed does not lead to reproducible results. An especially serious drawback of the known method is that PCR amplification does not provide any intact DNA fragments of uniform sequence, which are necessary for further analysis. Obtaining these requires time-consuming cloning of the amplified gene sections.

Yet another drawback of the method described in the prior art is the necessity of using the solvents phenol and chloroform, which pose a severe health risk.

One of the objects of this invention was thus to provide a method with which nucleic acids contained in biological matter can be stabilized against degradation and with which substances inhibiting the enzymatic manipulation of nucleic acids can be removed. In particular, a method was to be provided with which DNA can be reliably isolated from fecal specimens.

SUMMARY OF THE INVENTION

This object is established by means of a method of purifying, stabilizing and/or isolating nucleic acids contained in biological matter, wherein an adsorption matrix is added to a nucleic-acid-containing specimen of biological material in order to bind contaminants and the nucleic acids are subsequently separated if necessary from the bound contaminants. The nucleic-acid-containing specimen is brought into contact with the adsorption matrix either directly or after taking up the specimen in a liquid.

With the method of the invention the usability of nucleic acids - especially DNA—isolated from biological matter is improved markedly. Besides, the addition of the adsorption matrix means that both substances which damage nucleic acids and substances which inhibit the enzymatic manipulation thereof are largely removed. The nucleic acids stabilized by the method of the invention can thus be stored for extended periods of time. A further advantage is that amplification, eg, by means of PCR, of the nucleic acids treated by addition of an adsorption matrix leads to reproducible results. This reproducibility is essential with regard to the informative value of the results of the nucleic-acid analysis. The high quality of the nucleic acids purified by means of the method of the invention is evident, for example, in that they can be examined directly by way of sequencing or heteroduplex analysis. Cloning is unnecessary, and there is no need to use solvents which pose a health risk.

DETAILED DESCRIPTION

The adsorption matrix used in the method of the invention is of such nature that it can bind contaminants which damage nucleic acids and/or prevent the carrying out of enzymatic reactions and/or inhibit enzymatic reactions, eg, degradation products of hemoglobin such as bilirubin and its degradation products, and/or bile acids or salts thereof and other degradation products of plant or animal origin. It is of advantage to use an insoluble adsorption matrix as this is easier to separate from the specimen.

Good results are obtained with an adsorption matrix based on carbohydrates and/or polypeptides. An adsorption matrix based on carbohydrates is preferred, eg, an adsorption matrix which contains polysaccharides. Particular preference is given to an adsorption matrix which contains carbohydrates with $\alpha$- and/or $\beta$-gycosidic linkages, eg, starch, cellulose, glycogen and/or other biogenic or non-biogenic carbohydrates and derivatives or mixtures thereof.

The highest preference is given to flours, ie, essentially a mixture of cellulose, starch, lipids and salts or components thereof. Flours made from grain, maize, peas, soya and potatoes or components or mixtures thereof have, for example, proved suitable. For anyone versed in the art, it is self-evident that besides the flour sorts mentioned above, other kinds of flour or mixtures of several kinds of flour or components thereof can be used. The highest preference is given to potato flour or components thereof. Mixtures of purified carbohydrates such as cellulose and of flours such as potato flour are likewise suitable.

Another useful adsorption matrix is one based on carbohydrates together with soluble flour components, in particular components of one or more of the aforementioned flour sorts.

The amount of adsorption matrix added to the biological specimen depends mainly on the constitution of the specimen, ie, the quantity of contaminants. Good results are obtained if the adsorption matrix is added in a proportion by weight ranging from 0.05:1 to 100:1 relative to the specimen containing the nucleic acids. It is particularly preferable if the adsorption matrix is added in a quantity in the range from 0.1:1 to 10:1.

The nucleic-acid-containing specimen to be stabilized with the method of the invention originates from biological matter which contain contaminants that degrade nucleic acids or inhibit enzymatic reactions. It is preferable if the nucleic-acid-containing specimen is of fecal origin. It can, however, originate from other sources too, eg, from tissues of all kinds, bone marrow, human and animal body fluids such as blood, serum, plasma, urine, sperm, cerebrospinal fluid, sputum and smears, from plants, plant parts and extracts such as juices, from fungi, from microorganisms such as bacteria, from fossil or mummified specimens, soil samples, sewage sludge, waste water and foodstuffs. The contaminants contained in the specimen may be, eg, degradation products of hemoglobin such as bilirubin and its degradation products, and/or bile acids or salts thereof or degradation products thereof, but there may also be other kinds of contaminants.

The method has proved easier to implement if, prior to the addition of the adsorption matrix, the specimen is taken up into a buffer solution. The specimen can be incubated with the adsorption matrix at room temperature, and the period of incubation may be varied within wide limits. Following incubation, the adsorption matrix is separated from the specimen, eg, by means of centrifuging. Alternatively, the specimen can be mixed directly with the adsorption matrix, eg, in the case of liquid specimens. A further alternative is to pass the specimen over an adsorption matrix by way of centrifugation, by applying a vacuum and/or by means of gravity. It is preferable here if the adsorption matrix is packed in a column.

Treatment with the adsorption matrix significantly leads to increased stability of the nucleic acids contained in the specimen, and where they are subsequently isolated, to better reproducibility. This applies particularly if, following isolation, the nucleic acids are subjected to enzymatic manipulation, eg, amplification and/or restrictive cleavage. It is particularly preferable if amplification is carried out by means of PCR (Polymerase Chain Reaction), LCR (Ligase Chain Reaction), NASBA (Nucleic Acid Base Specific Amplification) or 3SR (Self Sustained Sequence Replication).

A particularly useful aspect of this invention is the analysis, detection or isolation of nucleic acids, especially DNA, contained in stool specimens. With the method of the invention, non-contaminated and amplifiable nucleic acids are obtained from fecal specimens and can be used to detect mutations, especially tumor-specific DNA mutations.

The method of the invention is of great significance for tumor diagnosis since it renders possible the specific detection of nuclear eukaryotic nucleic acids in the presence of contaminants, and large numbers of bacterial nucleic acids.

By using the method of the invention to analyze stool DNA, it is possible to diagnose tumors of the digestive tract, especially pancreatic and intestinal tumors, earlier and more accurately. Diagnosis is carried out, for example, by examining oncogenes and/or tumor suppressor genes on tumor-specific DNA mutations. Since the cells of tumors in the digestive tract continuously scale off into the stool, the method of the invention can be used to detect tumor-specific DNA mutations therein. It can also be used to monitor therapeutic treatments aimed at eliminating a tumor, and to carry out regular and reliable tumor-prevention examinations.

Unlike the test for occult blood in the stool, the only non-invasive routine test known from prior art for colorectal tumors, the method of the invention does not, or only very seldom, lead to false-positive results. Besides this, the detection of mutations in genes which mutate as early as the adenoma stage, ie, at a very early stage in tumor progression, makes a markedly earlier and more specific diagnosis possible than does the stool blood test. As suitable objects of mutational analyses use can be made, in particular, of the tumor suppressor gene APC (Adenomatous Polyposis Coli) (Fearon and Vogelstein (1990), Cell 61, 759–761) and the ras oncogene. Mutational analyses of these two genes in DNA from stool specimens are especially useful for detecting intestinal tumors, eg, tumors of the colon and pancreas. Besides the APC and the ras genes, it is of course possible to use other tumor-relevant genes as objects of analysis for the diagnosis of cancer.

Apart from tumor-relevant genes, non-translated, repetitive sections of the genome can also serve as object of analysis in cancer diagnosis. These so-called micro-satellite sections are amplified, and the band pattern obtained with gel electrophoresis compared with the band pattern of DNA taken from healthy body tissue in the same patient. Different band patterns may indicate the presence of a tumor.

A further application of the method of the invention is the exact identification of persons by means of forensic analysis of purified nucleic acids obtained from feces or body tissues. For this purpose, repetitive, polymorphous sections of the genome are amplified and the amplification products separated by means of electrophoresis. By comparing the resulting band patterns with the DNA patterns of other suspect or closely related persons, the person in question can be identified.

Another important application of the method according to the invention for isolating DNA from fecal specimens is for zoobiological population-genetical, evolution-genetical and botanical studies and research on animals and plants. Up till now, such studies have very often failed due to the rareness of an animal species or the improbability of finding the particular animals at a certain place. If the approximate whereabouts are known, feces left behind by the animals can be analyzed using the method of the invention and can provide important information on the degree to which the animals are related, on the paths they have travelled and on their eating habits. The analysis of fecal nucleic acids, eg, through detection of of micro-bacterial or viral nucleic acids, can also provide important diagnostic information on infections, for example of bacterial or viral nature.

A further object of this invention is a reagents kit for the stabilization and purification of nucleic acids contained in biological matter, comprising:

(a) a buffer suitable for taking up a specimen containing nucleic acids, and (b) an adsorption matrix for binding contaminants contained in biological matter.

The adsorption matrix may be provided in a packed and portioned form, eg, packed in a column such as a centrifugable mini-column.

It is preferable if the reagents kit contains additional means to purify nucleic acids, comprising, eg, mineral and/or organic carrier substances and maybe solutions, auxiliary agents and/or accessories. Mineral components of carrier substances can be, eg, porous or non-porous metal oxides or mixed metal oxides, eg, aluminium oxide, titanium dioxide or zirconium dioxide, silica gels, glass-based materials, eg, modified or non-modified glass particles or glass powder, quartz, zeolites, or mixtures of one or more of the above-mentioned substances. The carrier substance can, however, also contain organic components selected, eg, from latex particles, synthetic polymers such as polyethylene, polypropylene, polyvinylidene fluoride, especially ultra-high-molecular polyethylene or HD polyethylene, or mixtures of one or more of the aforementioned substances, which may also be modified with functional groups.

The carrier substance can, eg, take the form of particles with an average size of 0.1 $\mu$m to 1000 $\mu$m. Where porous carrier substances are used, an average pore size of 2 μm to 1000 μm is preferred. The carrier substance can, eg, take the form of loose particle beds, filter layers, eg, of glass, quartz or ceramic material, membranes, eg, membranes with a silica gel, fibers or fabrics of mineral carrier substances such as quartz or glass wool, or it can take the form of latices or fritted materials made from synthetic polymers.

The reagents kit can also contain suitable solutions such as wash solutions or buffer solutions to take up the specimen. An example of a buffer which is suitable to take up a specimen containing nucleic acids is a buffer system based on tris-HCl pH 8.5–9.5, EDTA and maybe NaCl. A particularly preferred buffer, especially for taking up stool specimens, contains 500 mM (=500 mmol/l) tris-HCl pH 9, 50 mM EDTA and 10 mM NaCl.

The reagents kit of the invention can also contain auxiliary agents such as enzymes and other means to manipulate nucleic acids, eg, at least one amplification primer and enzymes which are suitable for the amplification of nucleic acids, eg, a nucleic acid polymerase and/or at least one restriction endonuclease.

It is expedient if the primers for amplifying nucleic acids originate from the genes to be analyzed, eg, from oncogenes, tumor suppressor genes and/or micro-satellite sections. The enzymes and restriction endonucleases which are suitable for the amplification of nucleic acids are known and are commercially available.

The invention will now be explained on the basis of the following examples:

Example 1

Analysis of DNA from stool specimens

The following adsorption matrices were tested: immobilized bovine serum albumin (BSA), cellulose and potato starch (all from the company Sigma in Munich, Germany), and potato flour (company Honig, Postbus 45, 1540 AA Koog a/d Zaan, NL), which is essentially an insoluble mixture of cellulose, starch, lipids and salts.

Human stool specimens were collected, frozen and stored at −80° C. 200 mg of stool were homogenized in 600 μl of stool buffer solution (SBS: 500 mM tris-HCl pH 9.0, 50 mM EDTA, 10 mM NaCl). The homogenate was divided into four equal volumes; to each equal volume of homogenate 200 μl of SBS with 100 mg of the particular adsorption matrix were added. The mixture was shaken hard and then centrifuged twice, once at 500 g for 5 minutes and once at 13000 g for 5 minutes so as to precipate bacteria and other contaminants. After treating the clear supernatant with proteinase K in a concentration of 2.5 mg/ml, the DNA was purified using a DNA spin column (company Qiagen in Hilden, Germany) which is suitable for the purification of DNA from blood and tissue. The column was loaded and the washing steps performed in accordance with the manufacturer's specifications.

The DNA was then eluted from the spin column in a final volume of 150 μl of distilled water, and stored at −20° C. until needed. The yield of chromosomal DNA was determined by measuring the absorption at 260 nm.

All of the preparations showed comparable total-DNA amounts of 15–20 μg. On an analytical agarose gel, no differences were detected between the genomic DNA from preparations with and without adsorption matrix. Neither did the addition of adsorption matrix increase the yield of extracted chromosomal DNA.

To test the stability of the isolated nucleic acids, the DNA was examined after having been stored for a week. The results are shown in Table 1. The stabilized DNA specimens were obtained after using potato flour as adsorption matrix.

For the PCR amplification use was made of 3 μl of the purified chromosomal DNA in a total volume of 50 μl that contained 10 mM tris-HCl pH 8.3, 50 mM KCl, 1.5 mM $MgCl_2$, 30 mM each of dATP, dCTP, dGTP and dTTP, 400 nmol of each primer, 100 μg/ml BSA and 0.75 units of taq polymerase (AGS in Heidelberg, Germany).

To improve the sensitivity, nested PCR methods (cf. Jackson et al., (1991), in McPherson, N. J. Quirke, P. Taylor, G. R. (publ.), PCR—A Practical Approach, Oxford University press) were implemented using biotin-labeled nested primers. A PCR of DNA specimens purified in the absence of an adsorption matrix was blocked completely. By adding BSA, cellulose or potato starch as adsorption matrix, partially reproducible PCR results were obtained (Table 1).

When potato flour was used as adsorption matrix, reproducible PCR results were obtained for all the ten specimens analyzed. The PCR fragments were suitable for use in heteroduplex analysis and also for direct sequencing. To this end single-stranded DNA was prepared using streptavidin-coupled magnetic beads (company Dynal in Hamburg, Germany) in accordance with the manufacturer's specifications.

TABLE 1

Properties of nuclear DNA from stool

| Matrix | Loss[a] | PCR[b] |
|---|---|---|
| — | 80% | 0 |
| BSA | 60% | 3 |
| Cellulose | 60% | 4 |
| Potato starch | 60% | 4 |
| Potato flour | <5% | 10 |

[a]The DNA loss as a result of degradation was measured after a week's storage at −20° C. by means of analytical agarose gel electrophoresis and spectrophotometric analysis.
[b]A PCR was performed on DNA from ten different stool specimens. The number indicated is the number of specimens which could be analyzed by PCR.

Example 2

Purification of fecal specimens

Buffers used:

Buffer SBS: (see Example 1)

Buffer A: 5.6M guanidinium/HCl; 20% Tween 20

Buffer B: 10 mM tris-HCl pH 7.5; 100 mM NaCl; 70% ethanol

Buffer C: 10 mM tris-HCl pH 9.0; 0.5 mM EDTA 3 g of a frozen stool specimen were weighed out and mixed with 2 ml of buffer SBS by means of thorough vortexing. A column was then packed with a 1:1 mixture (w/w) of potato flour and cellulose and introduced into a 50 ml centrifugation tube. The specimen, taken up in buffer, was passed into the column and freed of contaminants by centrifuging at 500 rpm for 5 minutes.

0.125 ml of proteinase K stock solution (1.785 mg/ml) and 1.2 ml of buffer A were added to 1.2 ml of clarified specimen. After being mixed by means of vortexing for 1 minute, the specimen was incubated for 10 minutes at 70° C. Then 1.3 ml of absolute alcohol were added and the mixture shaken thoroughly. The solution was transferred to a QIAAMP (Company Qiagen) midi spin column with 15 ml collection tubes, and the nucleic acids bound on a silica matrix by means of centrifugation.

The bound nucleic acids were purified by washing twice with 2.5 ml of buffer B and then eluted from the QIAAAMP midi spin with 0.5 ml of buffer C. They were stored at −20° C. until needed.

When a PCR was carried out on the stored specimens as in Example 1, reproducible results were obtained.

We claim:

1. A method of purifying, stabilizing or isolating nucleic acids contained in a nuclei-acid-containing specimen of biological matter containing contaminants, the biological matter selected from human or animal tissues, bone marrow, plants, plant parts and extracts, fungi, microorganisms, fossil or mummified specimens, soil samples, sewage sludge, wastewater, feces, foodstuffs, or body fluids with the exception of whole blood, comprising adding an adsorption matrix to the nucleic-acid-containing specimen in order to bind the contaminants.

2. The method of claim 1, wherein the adsorption matrix is carbohydrate-based.

3. A method of purifying, stabilizing or isolating nucleic acids contained in a nucleic-acid-containing specimen of biological matter containing contaminants, comprising adding an insoluble, carbohydrate-based adsorption matrix to the nucleic-acid-containing specimen in order to bind the contaminants and not the nucleic acids thereto.

4. A method according to claim 2 or 3, wherein the adsorption matrix contains carbohydrates with α- or β-glycosidic linkages.

5. A method according to claim 2 or 3, wherein the adsorption matrix comprises starch, cellulose, glycogen, or other biogenic or non-biogenic carbohydrates or mixtures thereof.

6. A method according to claim 1 or 3, wherein the adsorption matrix is a flour made from grain, peas, maize, soya, potatoes or compounds or mixtures thereof.

7. The method of claim 6, wherein the adsorption matrix is potato flour or components thereof.

8. A method according to claim 1 or 3, wherein the adsorption matrix comprises carbohydrates in combination with soluble flour components.

9. A method according to claim 1 or 3, wherein the adsorption matrix comprises purified carbohydrates or flours.

10. A method according to claim 1 or 3, wherein the adsorption matrix comprises mixtures of cellulose and potato flour.

11. A method according to claim 1 or 3, wherein the adsorption matrix is added in a proportion by weight ranging from 0.05:1 to 100:1 relative to the nucleic-acid-containing specimen.

12. A method according to claim 3, wherein the nucleic-acid-containing specimen is selected from human or animal tissues, bone marrow, body fluids, plants, plant parts and extracts, fungi, microorganisms, fossil or mummified specimens, soil samples, sewage sludge, waste water, feces or foodstuffs.

13. A method according to claim 1 or 3, wherein the contaminants contained in the nucleic-acid-containing specimen are substances which have a damaging effect on nucleic acids or an inhibitory effect on enzymatic reactions.

14. A method according to claim 1 or 3, wherein the contaminants contained in the nucleic-acid-containing specimen are degradation products of hemoglobin, or bile acids or salts thereof.

15. A method according to claim 1 or 3, wherein the contaminants contained in the nucleic-acid-containing specimen are degradation products of plant or animal origin.

16. A method according to claim 1 or 3, wherein the nucleic-acid-containing-specimen is taken up into a buffer solution prior to the addition of the adsorption matrix.

17. A method according to claim 1 or 3, wherein the nucleic-acid-containing specimen is mixed directly with the adsorption matrix.

18. A method according to claim 1 or 3, wherein the nucleic-acid-containing specimen is passed over the adsorption matrix by means of centrifuging, applying a vacuum, or by means of gravity.

19. A method according to claim 1 or 3, wherein isolation is followed by direct analysis of the nucleic acids.

20. A method according to claim 1 or 3 wherein said isolation is followed by contacting said nucleic acids with an enzyme.

21. The method of claim 20, wherein the enzymatic manipulation comprises amplification or restriction cleavage.

22. The method of claim 21, wherein amplification is carried out by means of PCR (Polymerase Chain Reaction), LCR (Ligase Chain Reaction), NASBA (Nucleic Acid Base Specific Amplification) or 3SR (Self Sustained Sequence Replication).

23. The method of claim 1 or 3, further comprising analysis, detection, or isolation of nucleic acids contained in stool specimens.

24. The method of claim 23, further comprising the detection of DNA mutations.

25. The method of claim 23, further comprising detection or isolation of eukaryotic nuclear nucleic acids.

26. The method of claim 24, further comprising detection or isolation of eukaryotic nuclear nucleic acids.

27. The method of claim 25, further comprising diagnosis of a digestive tract tumor.

28. The method of claim 27, wherein the digestive tract tumor is a pancreatic tumor and an intestinal tumor.

29. The method of claim 27, further comprising examining oncogenes, tumor suppressor genes or microsatellite sections.

30. The method of claim 25, wherein said eukaryotic nuclear nucleic acids occur in plants or animals.

31. The method of claim 23, further comprising detecting microbial or viral nucleic acids contained in stool specimens.

32. The method of claim 31, further comprising diagnosing bacterial and viral infections.

33. A method according to claim 1 or 2, further comprising proving interrelations or forensic identification of individual persons.

34. A reagent kit for the purification and stabilization of nucleic acids contained in a nucleic acid-containing specimen of biological matter containing contaminants, comprising:
    (a) a buffer suitable for taking up the nucleic-acid-containing specimen, and
    (b) an insoluble, carbohydrate-based adsorption matrix for binding the contaminants and not the nucleic acids.

35. The reagent kit of claim 34, further comprising means to further purify the nucleic acids.

36. The reagent kit of claim 34, wherein the means to further purify the nucleic acids comprise a mineral or organic carrier substance.

37. The reagent kit of claim 35, wherein the means to further purify the nucleic acids comprise at least one amplification primer or enzyme for contacting to said nucleic acids.

38. The reagent kit of claim 36, wherein the carrier substance comprises a component selected from the group of porous or non-porous metal oxides, mixed metal oxides, silica gels, glass- or quartz-based materials, zeolites or mixtures thereof.

39. The reagent kit of claim 36, wherein the carrier substance contains an organic component selected from the group of latex, synthetic polymers and mixtures thereof.

40. The reagent kit of claim 39, wherein the organic component is modified.

41. A reagent kit according to claim 36, wherein the carrier substance is in the form of particles with an average size of 0.1 µm to 1000 µm.

42. A reagent kit according to claim 36, wherein the carrier substance exhibits pores with an average size of 2 µm to 1000 µm.

43. A reagent kit according to claim 36, wherein the carrier substance is in the form of loose particle beds, filter layers, membranes, fabrics, fibers or fritted materials.

44. A reagent kit according to claim 34, wherein the adsorption matrix is packed in a column.

* * * * *

UNITED STATES PATENT AND TRADEMARK OFFICE
CERTIFICATE OF CORRECTION

PATENT NO. : 6,084,091
DATED : Jul. 4, 2000
INVENTOR(S) : Müller et al

It is certified that error appears in the above-indentified patent and that said Letters Patent is hereby corrected as shown below:

In column 1, line 14, change "impedance" to -- importance --.
In column 6, line 66, after "spin" insert -- column --.
In column 7, line 5, change "nuclei-acid" to -- nucleic-acid --.

Signed and Sealed this

Seventeenth Day of April, 2001

Attest:

NICHOLAS P. GODICI

Attesting Officer     Acting Director of the United States Patent and Trademark Office